(12) United States Patent
Bär et al.

(10) Patent No.: US 7,463,039 B2
(45) Date of Patent: *Dec. 9, 2008

(54) PROBE FOR ELECTRICAL MEASUREMENT METHODS, ESPECIALLY EDDY CURRENT MEASUREMENTS

(75) Inventors: Ludwig Bär, Erlangen (DE); Werner Heinrich, Bärenklau (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

This patent is subject to a terminal disclaimer.

(21) Appl. No.: 10/563,947

(22) PCT Filed: Jun. 23, 2004

(86) PCT No.: PCT/EP2004/006792

§ 371 (c)(1),
(2), (4) Date: Jun. 27, 2006

(87) PCT Pub. No.: WO2005/005976

PCT Pub. Date: Jan. 20, 2005

(65) Prior Publication Data

US 2007/0182422 A1    Aug. 9, 2007

(30) Foreign Application Priority Data

Jul. 9, 2003    (EP)    ................................. 03015494

(51) Int. Cl.
    *G01R 27/26*    (2006.01)
    *G01N 27/72*    (2006.01)
(52) U.S. Cl. .................. 324/600; 324/696; 324/220
(58) Field of Classification Search ........... 324/537, 324/696, 230, 232, 239, 242
    See application file for complete search history.

(56) References Cited

U.S. PATENT DOCUMENTS

| | | | |
|---|---|---|---|
| 4,438,399 A | * | 3/1984 | Schnabl et al. ........... 324/220 |
| 5,021,738 A | * | 6/1991 | Vernon et al. ............. 324/232 |
| 5,315,234 A | | 5/1994 | Sutton, Jr. et al. |
| 5,389,876 A | | 2/1995 | Hedengren et al. |
| 6,002,251 A | | 12/1999 | Sun |

FOREIGN PATENT DOCUMENTS

| | | |
|---|---|---|
| DE | 197 48 556 A1 | 5/1999 |
| JP | 10197492 A | 7/1998 |
| WO | WO 03/060530 A1 | 7/2003 |

* cited by examiner

*Primary Examiner*—Vincent Q Nguyen

(57) ABSTRACT

When using a rigid substrate eddy current probe to measure a non-planer test piece, the probe must be adapted to the test piece shape in order to avoid incorrect measurement values. Disclosed is a probe which is configured in a flexible manner via a flexible substrate so as to be adjustable to different radii of curvature of a test piece. Furthermore the probe lining is also embodied in an elastic manner.

11 Claims, 1 Drawing Sheet

PROBE FOR ELECTRICAL MEASUREMENT METHODS, ESPECIALLY EDDY CURRENT MEASUREMENTS

CROSS REFERENCE TO RELATED APPLICATION

This application is the US National Stage of International Application No. PCT/EP2004/006792, filed Jun. 23, 2004 and claims the benefit thereof. The International Application claims the benefits of European Patent application No. 03015494.2 EP filed Jul. 9, 2003, both of the applications are incorporated by reference herein in their entirety.

FIELD OF THE INVENTION

The invention is based on a probe for electrical measurement methods according to the claims.

BACKGROUND OF THE INVENTION

DE 197 48 556 A1 discloses a probe for an eddy current measurement with a ferromagnetic signal amplification, the signal amplification being produced by a rigid ferritic core. With a probe formed by a rigid substrate on which planar coils are mounted, test pieces with a planar surface can be measured. In the case of non-planar surfaces, the probe must be adapted in its shape to a surface of the test piece; otherwise, incorrect measured values are obtained.

A probe with eddy current measurement with ferromagnetic signal amplification for planar test pieces is also known from U.S. Pat. No. 6,002,251.

U.S. Pat. No. 5,389,876 discloses a probe for an eddy current measurement, which however produces only weak signals.

SUMMARY OF THE INVENTION

The object of the invention is therefore to present a probe for electrical measurement methods which can be used for variously curved surfaces of the test piece.

The object is achieved by the probe with the substrate being formed permanently elastically.

Further advantageous refinements of the probe according to the invention are mentioned in the subclaims.

The probe can be adapted to radii of curvature of, for example, 50 mm or greater.

The flexibility is advantageously achieved by a substrate that is formed by a flexible film being used for the probe, advantageously polyimide.

For example, two coils, especially planar coils, especially of copper, are advantageously mounted on the flexible film as electrical components.

The flexibility of the probe is also maintained by a permanently elastic backing of the electrical components.

A polymer film which is filled with a ferrite is advantageously used for the backing, so that a ferromagnetic signal amplification is advantageously possible.

Similarly, thin flexible sheets of ferrite may be used.

A casting compound with ferrite particles, the casting compound being permanently elastically deformable, may also be used here.

BRIEF DESCRIPTION OF THE DRAWINGS

Exemplary embodiments of the invention are represented in a simplified and schematic form in the drawings, in which.

DETAILED DESCRIPTION OF THE INVENTION

Figure 1:
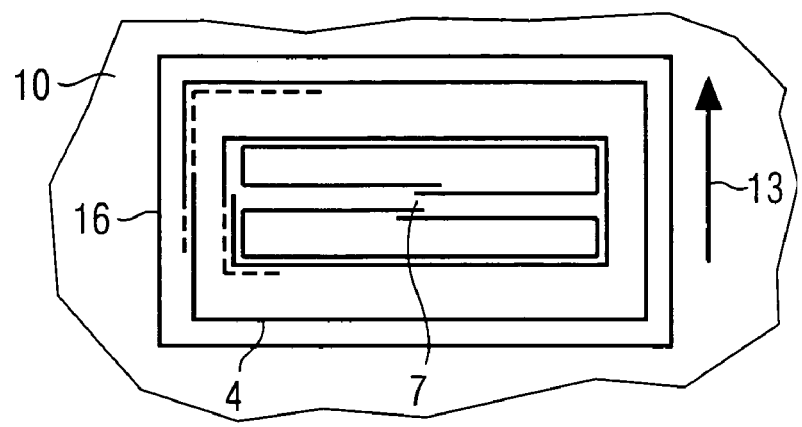
FIG. 1 shows an arrangement of an exciter and a signal coil.

FIG. 1 shows an exciter coil 4 and a signal coil 7 as electrical components in their arrangement in one plane according to the prior art.

The signal coil 7 is, for example, surrounded by the exciter coil 4. With respect to the further exemplary construction of the exciter coil 4, signal coil 7 and an evaluation system with a probe, reference is made to DE 197 48 556 A1, which is expressly intended to form part of this disclosure.

The exciter coil 4 and signal coil 7 are electrically separated from each other. The signal coil 7 is in this example designed as a differential probe. The local resolution is determined by the distance between the the two coil sections, the so-called baseline.

The exciter winding 4 encloses the coil sections of the signal coil 7, for example symmetrically, so that a compensation of the exciter field is ensured. The exciter winding 4 and the signal coil 7 consequently lie in one plane or on the same surface of the substrate 16. Exemplary embodiments of probes are:

An XXL probe has a baseline of 3.3 mm, an exciter coil with 21 windings and a signal coil with 8 windings.

An S probe has a baseline of 2.3 mm, an exciter coil with 9 windings and a signal coil with 5 windings.

Figure 2:
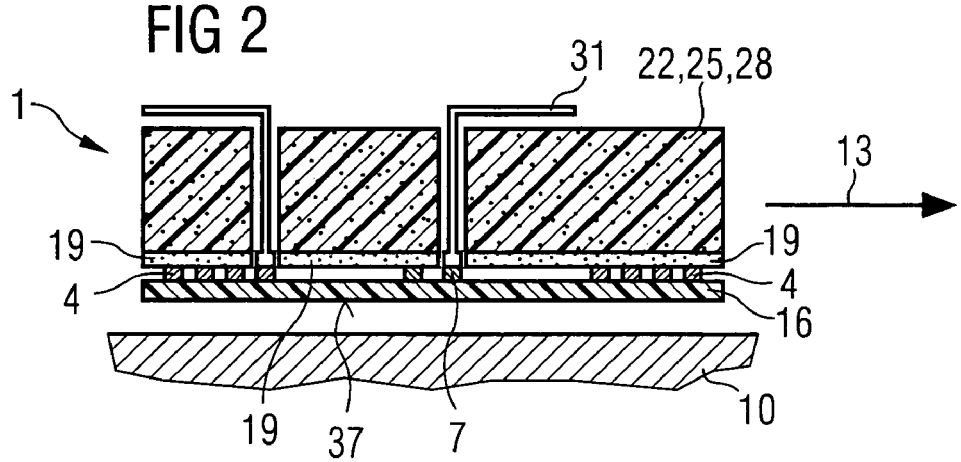
FIG. 2 shows a first exemplary embodiment of a probe according to the invention.

A probe, which comprises, inter alia, the exciter coil 4 and signal coil 7, is moved in a scanning direction 13, identified by an arrow, over a surface of a test piece 10 (indicated by a dashed outline), the probe 1 coming to rest on the test piece 10 with a resting surface 37 (FIG. 2). The test piece 10 contains defects, for example in the form of cracks, which influence a magnetic signal of the exciter coil 4, whereby the defects in the interior of the test piece 10 and on its surface can be established.

FIG. 2 shows a first exemplary embodiment of a probe 1 for electrical measurement methods according to the present invention. A film, which is flexible and, for example, also elastic, especially permanently elastic, is used for example as the substrate 16, which rests directly on the test piece. A polyimide film is preferably used.

Permanent elasticity means that the mechanical elasticity is maintained at least over the service life of the probe 1. On the substrate 16, the exciter coil 4 and the signal coil 7 are arranged, for example, in a planar manner, i.e. the coil comprises only one conductor track which runs only in one plane. The coils 4, 7, as electrical components, may be mounted on the film 16 by means of a galvanic process or a wet-chemical process.

On the substrate 16 and on or around the coil 4, 7, there is applied for example, but not necessarily, an adhesive 19, which bonds the backing 22 to the substrate 16.

The backing 22 is of an elastic, especially permanently elastic, form.

Preferably used as the material for the backing 22 is a ferritic and/or other magnetic (ferromagnetic, strongly paramagnetic) material for signal amplification, in particular for ferromagnetic signal amplification, for example with a permeability $\mu$ of up to 100. Leading through the backing 22 there is, for example, at least one electrical lead 31 for the coil 4, 7 for a measuring system according to DE 197 48 556 A1.

An elastic, especially permanently elastic, casting compound filled with ferrite particles or a gas-filled material, in particular plastic or rubber, may be used as the backing 22.

The polyimide film 16 has, for example, a thickness of 25 μm, the copper coil has a thickness of 17 μm, the adhesive extends over a thickness of about 30 μm, and the polymer film filled with ferrite extends over a thickness of 200-600 μm.

This stack of layers comprising the substrate 16 and the backing 22 remains sufficiently flexible, so that the stack of layers can adapt itself without any problem to different radii of curvature of the test piece 10 of, for example, 50 mm or more.

Figure 3:
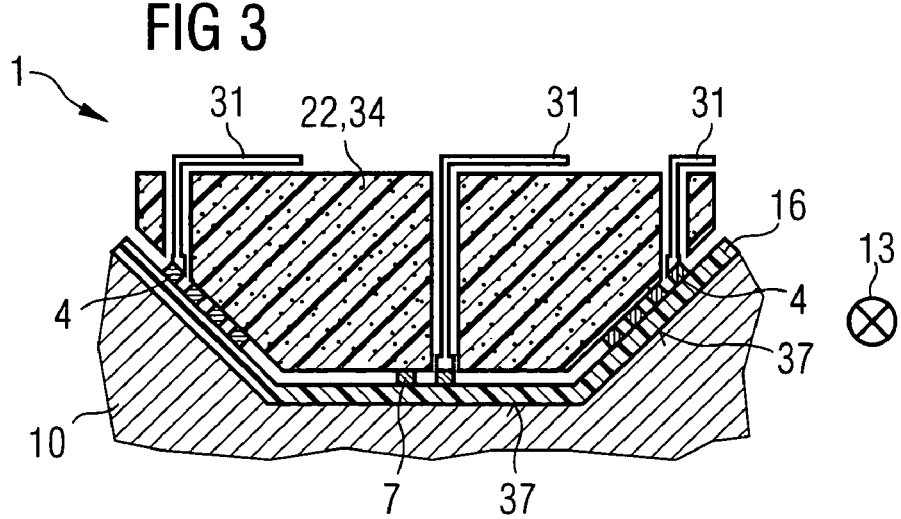
FIG. 3 shows a further exemplary embodiment of a probe formed according to the invention.

FIG. 3 shows a further exemplary embodiment of a planar probe 1 formed according to the invention.

The backing 22 may also be ensured by a casting material 34, in which ferrite powder is mixed. The average diameter of the ferrite particles is, for example, about 10 μm. The casting compound is elastically, especially permanently elastically, deformable, and remains so after a curing process, so that a flexibility of the probe 1 is permanently ensured.

The probe 1 is made to be of such a size that it covers the entire region to be examined of the test piece 10, for example a trough, as represented for example in FIG. 3, so that the region to be examined is examined in one scan, that is by moving the probe 1 once.

Such troughs occur for example in the case of blade roots of a fir-tree-shaped turbine blade.

As electrical measurement methods, the probe 1, which has two coils 4, 7 or only one coil and a ferromagnetic signal amplification 22, can be used for eddy current measurement, which serves, for example, the purpose of detecting defects on metallic components 10.

The invention claimed is:

1. An eddy current probe for electrical measurement methods, comprising:
   a substrate with a resting surface and the resting surface comes to lie on a test piece;
   two electrical components mounted on the substrate such that the probe with the substrate is flexible and the probe with the substrate adapts itself to a different radii of curvature of the test piece;
   a backing with a ferritic and/or magnetic material that at least partly covers at least one electrical component and is formed elastically;
   an exciter coil as a first electrical component; and
   a signal coil as the second electrical component,
   wherein the exciter coil encloses a coil section of the signal coil and the signal coil and the exciter winding lie in one plane or on a surface of the substrate.

2. The eddy current probe as claimed in claim 1, wherein the substrate is a flexible film.

3. The eddy current probe as claimed in claim 2, wherein the film is formed from polyimide.

4. The eddy current probe as claimed in claim 1, wherein the backing is formed by an elastic, sheet of a ferritic material.

5. The eddy current probe as claimed in claim 1, wherein the backing is formed by a permanently elastic casting compound filled with ferrite particles.

6. The eddy current probe as claimed in claim 1, wherein the probe has as an electrical component that is a coil and is arranged on the substrate in a planar manner.

7. The eddy current probe as claimed in claim 1, wherein the probe has a ferromagnetic signal amplification.

8. The eddy current probe as claimed in claim 1, wherein the probe is adaptable to radii of curvature of up to 50 mm.

9. The eddy current probe as claimed in claim 1, wherein the backing is a gas-filled material.

10. The eddy current probe as claimed in claim 1, wherein the exciter coil and the signal coil are arranged in one plane.

11. The eddy current probe as claimed in claim 1, wherein a region to be examined is covered by the probe.

* * * * *